(12) United States Patent
Bergström et al.

(10) Patent No.: US 6,706,710 B2
(45) Date of Patent: Mar. 16, 2004

(54) FORM OF (R)-N-[5-METHYL-8-(4-METHYLPIPERAZIN-1-YL)-1,2,3,4-TETRAHYDRO-2-NAPHTHYL]-4-MORPHOLINOBENZAMIDE

(75) Inventors: Per-Olov Bergström, Johanneshov (SE); Martin Hedberg, Södertälje (SE); Mona Lindström, Södertälje (SE); Erica Ståhle, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/333,286

(22) PCT Filed: Jul. 17, 2001

(86) PCT No.: PCT/SE01/01643

§ 371 (c)(1),
(2), (4) Date: Jan. 17, 2003

(87) PCT Pub. No.: WO02/08212

PCT Pub. Date: Jan. 31, 2002

(65) Prior Publication Data

US 2003/0166653 A1 Sep. 4, 2003

(51) Int. Cl.[7] ..................... A61K 31/5327; A61P 25/22; C07D 413/12

(52) U.S. Cl. ..................................... 514/235.8; 544/121
(58) Field of Search ........................ 544/121; 514/235.8

(56) References Cited

U.S. PATENT DOCUMENTS 6,124,283 A * 9/2000 Berg et al. ................... 544/121
6,291,458 B1 * 9/2001 Berg et al. ................... 544/121

FOREIGN PATENT DOCUMENTS

WO 9905134 2/1999
WO 0043378 7/2000

* cited by examiner

Primary Examiner—Robert W. Ramsuer
(74) Attorney, Agent, or Firm—White & Case LLP

(57) ABSTRACT

This invention relates to a novel form of a scrotonin h5-HT$_{1B}$-receptor antagonist, namely a novel form of a salt of (R)-N-[5-methyl-8-(4-methylpiperazin-1-yl)-1,2,2,4-tetrahydro-2-naphtyl]-4-morpholinobenzamide referred to as (R)-N-[5-methyl-8-(4-methylpiperazin-1-yl)-1,2,3,4-tetrahydro-2-naphtyl]-4-morpholinobenzamide monohydrobromide Form A. The invention also relates to processes for preparation of said of Form A, which form has a potential use after suitable pharmaceutical formulation in medical treatment, preferably in CNS disorders, over active bladder or vasospam, or growth control of tumors.

17 Claims, 2 Drawing Sheets

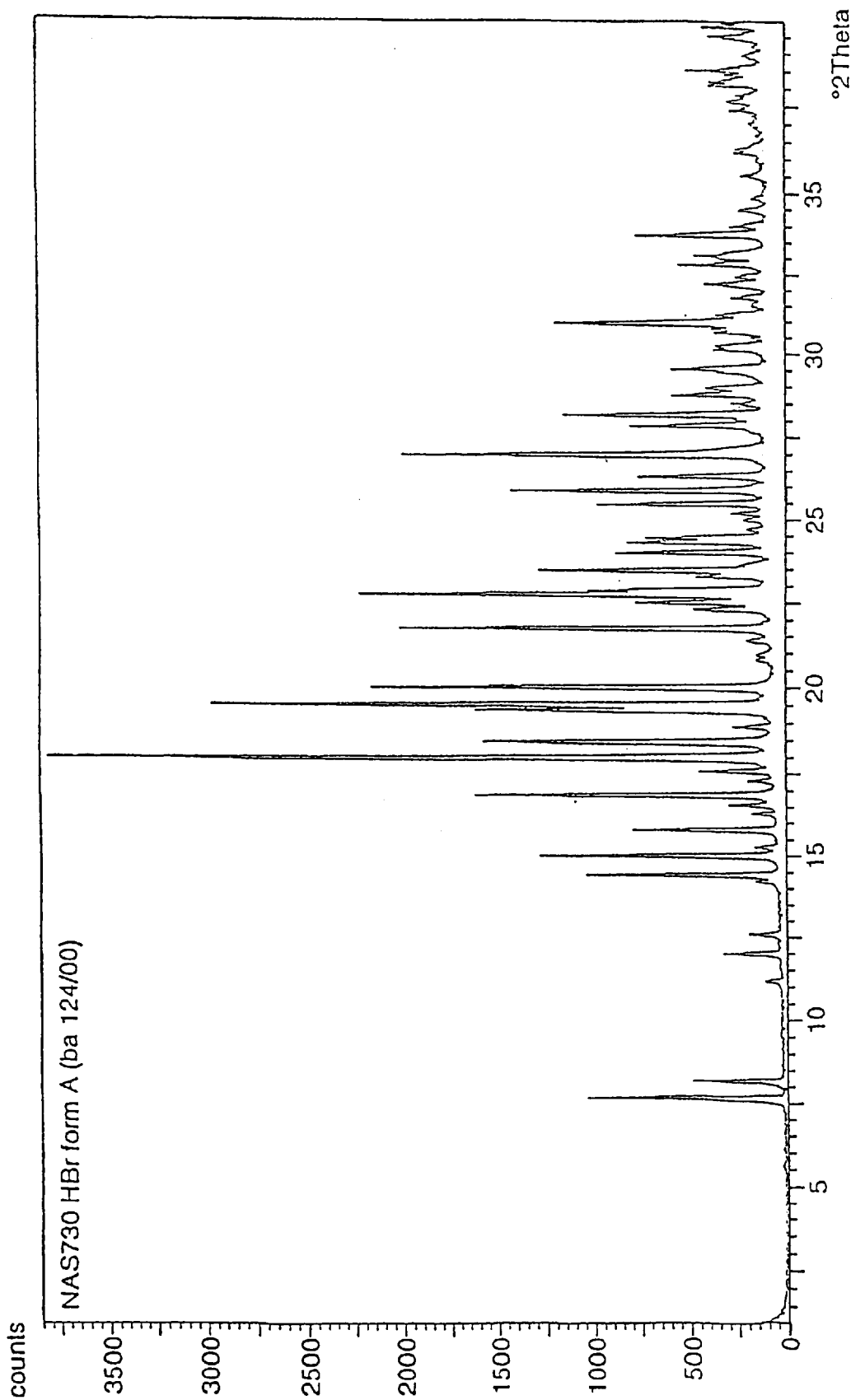

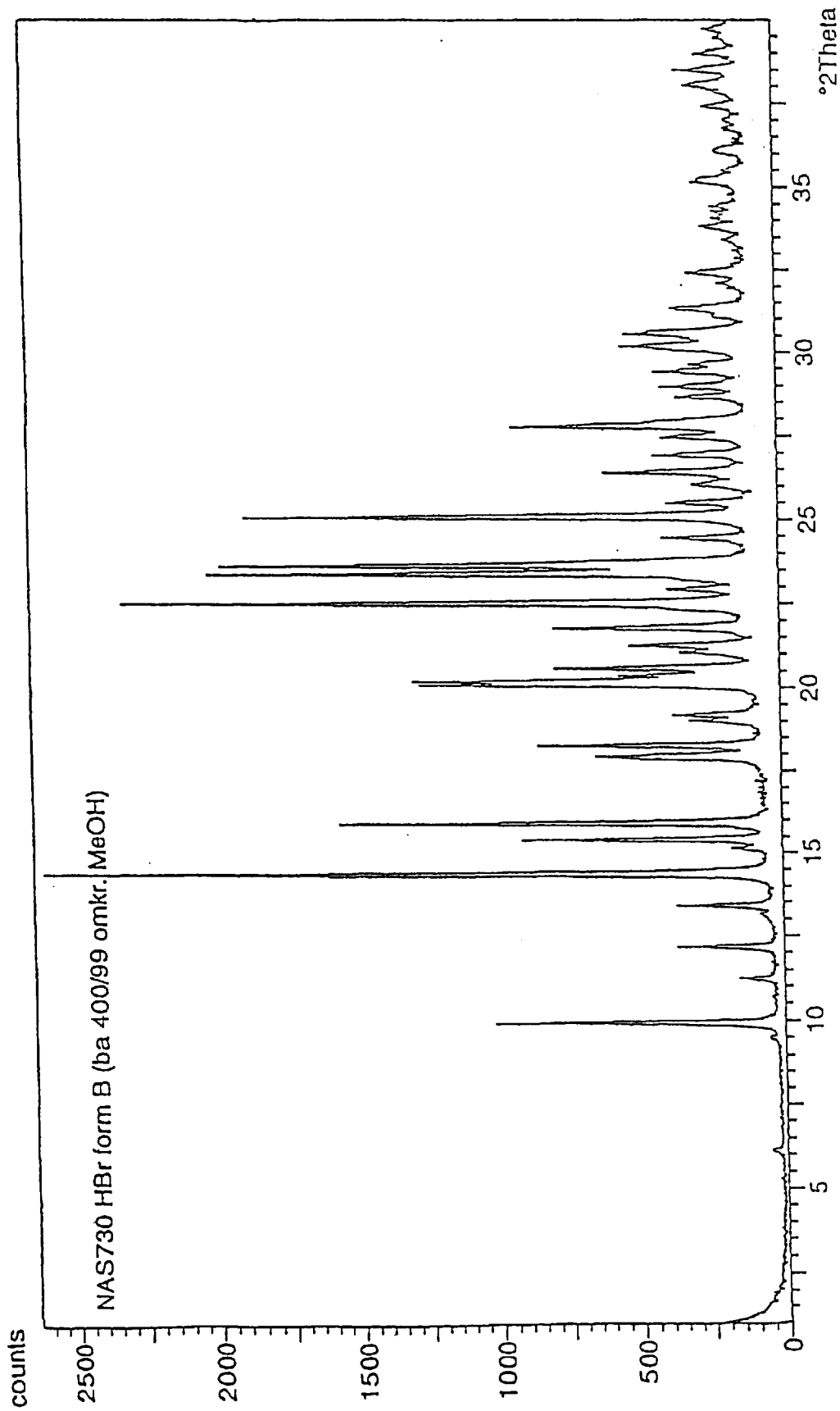

FORM OF (R)-N-[5-METHYL-8-(4-METHYLPIPERAZIN-1-YL)-1,2,3,4-TETRAHYDRO-2-NAPHTHYL]-4-MORPHOLINOBENZAMIDE

FIELD OF THE INVENTION

This invention relates to a novel form of a serotonin h5-$HT_{1B}$-receptor antagonist, namely a novel form of a salt of (R)-N-[5-methyl-8-(4-methylpiperazin-1-yl)-1,2,3,4-tetrahydro-2-naphtyl]-4-morpholinobenzamide referred to as (R)-N-[5-methyl-8-(4-methylpiperazin-1-yl)-1,2,3,4-tetrahydro-2-naphtyl]-4-morpholinobenzamide monohydrobromide Form A. The invention also relates to processes for production of said Form A, which form has a potential use after suitable pharmaceutical formulation in medical treatment.

PRIOR ART

[5-Methyl-8-(4-methylpiperazin-1-yl)-1,2,3,4-tetrahydro-2-naphtyl]-4-morpholinobenzamide, both the (R)- and (S)-enantiomer and the racemate and their methods of preparation are disclosed in WO 99/05134.

BACKGROUND OF THE INVENTION

Various central nervous system disorders such as depression, anxiety, etc. appear to involve the disturbance of the neurotransmitters noradrenaline (NA) and/or 5-hydroxytryptamine(5-HT), the latter also known as serotonin. The drugs most frequently used in the treatment of depression are believed to act by improving the neurotransmission of either or both of these physiological agonists. It appears that the enhancement of 5-HT neurotransmission primarily affects the depressed mood and anxiety, whereas the enhancement of noradrenaline neurotransmission affects the retardation symptoms occurring in depressed patients.

Serotonin, or 5-HT, activity is thought to be involved in many different types of psychiatric disorders. For instance it is thought that an increase in 5-HT activity is associated with anxiety, while a decrease in 5-HT release has been associated with depression. Serotonin has in addition been implicated in such diverse conditions as eating disorders, gastrointestinal disorders, cardiovascular regulation and sexual behaviour.

The compound N-[5-methyl-8-(4-methylpiperazin-1-yl)-1,2,3,4-tetrahydro-2-naphtyl]-4-morpholinobenzamide (both enantiomers as well as the racemate) has an extremely low solubility in water and a slow release rate which rate is pH dependent, i.e. the rate is different in the stomach and the intestines. From a pharmaceutical formulation point of view it is very difficult to dissolve the base rapidly enough and maintain the same dissolved in the gastric juice until a sufficient amount of substance has been absorbed.

DISCLOSURE OF THE INVENTION

The object of the invention is a novel form of a salt of (R)-N-[5-methyl-8-(4-methylpiperazin-1-yl)-1,2,3,4-tetrahydro-2-naphtyl]-4-morpholinobenzamide, namely (R)-N-[5-methyl-8-(4-methylpiperazin-1-yl)-1,2,3,4-tetrahydro-2-naphtyl]-4-morpholinobenzamide monohydrobromide Form A, which is a specific crystal modification of (R)-N-[5-methyl-8-(4-methylpiperazin-1-yl)-1,2,3,4-tetrahydro-2-naphtyl]-4-morpholinobenzamide monohydrobromide.

Another object of the invention is a process which reproducibly gives (R)-N-[5-methyl-8-(4-methylpiperazin-1-yl)-1,2,3,4-tetrahydro-2-naphtyl]-4-morpholinobenzamide monohydrobromide Form A. In addition it has been shown that (R)-N-[5-methyl-8-(4-methylpiperazin-1-yl)-1,2,3,4-tetrahydro-2-naphtyl]-4-morpholinobenzamide monohydrobromide can crystallize in other crystalline forms, for example Form B.

(R)-N-[5-methyl-8-(4-methylpiperazin-1-yl)-1,2,3,4-tetrahydro-2-naphtyl]-4-morpholinobenzamide monohydrobromide Form A is a crystal modification form of (R)-N-[5-methyl-8-(4-methylpiperazin-1-yl)-1,2,3,4-tetrahydro-2-naphtyl]-4-morpholinobenzamide monohydrobromide, which has several advantageous properties:

it has a satisfactory solubility in water;

it has a satisfactory thermal stability;

it is non-hygroscopic;

it has a good stability against light exposure.

It is predicted that these advantageous properties will lead to satisfactory chemical stability and long shelf life both for the pure substance and for pharmaceutical dosage forms containing (R)-N-[5-methyl-8-(4-methylpiperazin-1-yl)-1,2,3,4-tetrahydro-2-naphtyl]-4-morpholinobenzamide monohydrobromide Form A. Consequently, there may be fewer demands on packages, in particular on the water permeability and light transmission. Packages can thus be made of materials that are less complicated and more environmentally friendly, for instance blister packs can be made of transparent material so that the tablets can be visible and the total package is smaller than in the case of aluminium blister packs.

Characteristics of (R)-N-[5-methyl-8-(4-methylpiperazin-1-yl)-1,2,3,4-tetrahydro-2-naphtyl]-4-morpholinobenzamide monohydrobromide Form A The novel form of a salt of (R)-N-[5-methyl-8-(4-methylpiperazin-1-yl)-1,2,3,4-tetrahydro-2-naphtyl]-4-morpholinobenzamide of the invention, i.e. (R)-N-[5-methyl-8-(4-methylpiperazin-1-yl)-1,2,3,4-tetrahydro-2-naphtyl]-4-morpholinobenzamide monohydrobromide Form A, can be distinguished from other forms by methods such as Powder X-ray diffractometry (XRPD).

DETAILED DESCRIPTION OF THE INVENTION

In a first aspect, the invention thus provides (R)-N-[5-methyl-8-(4-methylpiperazin-1-yl)-1,2,3,4-tetrahydro-2-naphtyl]-4-morpholinobenzamide monohydrobromide Form A, preferably substantially crystallographically pure (R)-N-[5-methyl-8-(4-methylpiperazin-1-yl)-1,2,3,4-tetrahydro-2-naphtyl]-4-morpholinobenzamide Form A. A crystallographically pure form is a crystal modification that, as far as can be judged from XRPD measurements, contains no peaks from other crystal modifications. The term "substantially crystallographically pure (R)-N-[5-methyl-8-(4-methylpiperazin-1-yl)-1,2,3,4-tetrahydro-2-naphtyl]-4-morpholinobenzamide monohydrobromide Form A" should thus be understood as (R)-N-[5-methyl-8-(4-methylpiperazin-1-yl)-1,2,3,4-tetrahydro-2-naphtyl]-4-morpholinobenzamide monohydrobromide Form A containing only small amounts of any other crystalline form of (R)-N-[5-methyl-8-(4-methylpiperazin-1-yl)-1,2,3,4-tetrahydro-2-naphtyl]-4-morpholinobenzamide monohydrobromide; preferably not more than 10% and most preferably not more than 3%, of any other crystalline form of (R)-N-[5-methyl-8-(4-methylpiperazin-1-yl)-1,2,3,4-tetrahydro-2-naphtyl]-4-morpholinobenzamide monohydrobromide. The term "form" is in this context equivalent to the term "crystal modification".

(R)-N-[5-methyl-8-(4-methylpiperazin-1-yl)-1,2,3,4-tetrahydro-2-naphtyl]-4-morpholinobenzamide monohydrobromide Form A can be characterized by the X-ray powder diffraction pattern:

| Form A | | | | | |
|---|---|---|---|---|---|
| d-value (Å) | Relative intensity | d-value (Å) | Relative intensity | d-value (Å) | Relative intensity |
| 11.7 | vs | 4.24 | vw | 3.09 | w |
| 10.9 | s | 4.16 | vw | 3.03 | w |
| 8.0 | w | 4.10 | s | 2.97 | w |
| 7.4 | m | 3.99 | w | 2.90 | m |
| 7.1 | w | 3.96 | m | 2.87 | w |
| 6.3 | w | 3.92 | vs | 2.82 | vw |
| 6.2 | s | 3.89 | m | 2.79 | vw |
| 5.9 | s | 3.83 | m | 2.74 | w |
| 5.8 | vw | 3.80 | s | 2.71 | w |
| 5.6 | m | 3.71 | m | 2.66 | w |
| 5.5 | vw | 3.67 | m | 2.64 | vw |
| 5.4 | m | 3.65 | m | 2.61 | vw |
| 5.3 | vs | 3.61 | vw | 2.58 | vw |
| 5.1 | vw | 3.57 | vw | 2.53 | vw |
| 5.1 | m | 3.54 | w | 2.48 | vw |
| 4.95 | vs | 3.50 | m | 2.41 | vw |
| 4.82 | s | 3.45 | s | 2.39 | vw |
| 4.71 | w | 3.39 | m | 2.38 | vw |
| 4.60 | s | 3.31 | s | 2.36 | vw |
| 4.56 | vs | 3.21 | m | 2.34 | vw |
| 4.45 | vs | 3.17 | m | 2.28 | vw |
| 4.28 | vw | 3.11 | m | 2.27 | vw |

Preparation of (R)-N-[5-methyl-8-(4-methylpiperazin-1-yl)-1,2,3,4-tetrahydro-2-naphtyl]-4-morpholinobenzamide monohydrobromide Form A In a further aspect, the invention relates to a process for the preparation of (R)-N-[5-methyl-8-(4-methylpiperazin-1-yl)-1,2,3,4-tetrahydro-2-naphtyl]-4-morpholinobenzamide monohydrobromide Form A. (R)-N-[5-methyl-8-(4-methylpiperazin-1-yl)-1,2,3,4-tetrahydro-2-naphtyl]-4-morpholinobenzamide monohydrobromide Form A may be prepared under controlled conditions from a mixture of one or more organic solvents. It is preferred to use a mixture of organic solvents, which is miscible with water. The optimal ratio or organic solvents in the mixture to obtain (R)-N-[5-methyl-8-(4-methylpiperazin-1-yl)-1,2,3,4-tetrahydro-2-naphtyl]-4-morpholinobenzamide monohydrobromide Form A is strongly dependent on the characteristics of the chosen organic solvents and the process conditions e.g. the temperature, the pressure and the solubility of (R)-N-[5-methyl-8-(4-methylpiperazin-1-yl)-1,2,3,4-tetrahydro-2-naphtyl]-4-morpholinobenzamide monohydrobromide in each of the solvents, as well as in the mixture of the solvents and their content of water.

In particular, (R)-N-[5-methyl-8-(4-methylpiperazin-1-yl)-1,2,3,4-tetrahydro-2-naphtyl]-4-morpholinobenzamide monohydrobromide Form A may be prepared by:

(i) partly dissolving any non-A form of (R)-N-[5-methyl-8-(4-methylpiperazin-1-yl)-1,2,3,4-tetrahydro-2-naphtyl]-4-morpholinobenzamide monohydrobromide in organic solvent(s) optionally containing a minor amount of water and stirring until Form A is formed, or by (ii) reaction crystallizing (R)-N-[5-methyl-8-(4-methylpiperazin-1-yl)-1,2,3,4-tetrahydro-2-naphtyl]-4-morpholinobenzamide or a salt different form (R)-N-[5-methyl-8-(4-methylpiperazin-1-yl)-1,2,3,4-tetrahydro-2-naphtyl]-4-morpholinobenzamide monohydrobromide with a buffering acidic salt of hydrobromic acid in organic solvent(s) optionally containing a minor amount of water; or by (iii) crystallizing from a solution of (R)-N-[5-methyl-8-(4-methylpiperazin-1-yl)-1,2,3,4-tetrahydro-2-naphtyl]-4-morpholinobenzamide monohydrobromide in a mixture of organic solvent(s) and water whereby crystals of (R)-N-[5-methyl-8-(4-methylpiperazin-1-yl)-1,2,3,4-tetrahydro-2-naphtyl]-4-morpholinobenzamide monohydrobromide Form A are formed spontaneously; or when crystals are not formed spontaneously, followed by 1) cooling the mixture; 2) evaporating some of the solvent or 3) mixing with a precipitating solvent whereby crystals of (R)-N-[5-methyl-8-(4-methylpiperazin-1-yl)-1,2,3,4-tetrahydro-2-naphtyl]-4-morpholinobenzamide monohydrobromide Form A are formed.

Method (i) is a transformation of polymorphs in slurry. Any non-A form of (R)-N-[5-methyl-8-(4-methylpiperazin-1-yl)-1,2,3,4-tetrahydro-2-naphtyl]-4-morpholinobenzamide monohydrobromide, e.g. amorphous material or for instance (R)-N-[5-methyl-8-(4-methylpiperazin-1-yl)-1,2,3,4-tetrahydro-2-naphtyl]-4-morpholinobenzamide monohydrobromide Form B, is initially partly dissolved in organic solvent(s) optionally containing a minor amount of water and stirred until the desired Form A is formed. The process comprises a transformation in the slurry without a complete dissolution of the starting material. Such transformation may occur, as it is known in the art, when there exists a form with higher thermodynamic stability than at the prevailing conditions. The driving force for the process is the normally lower solubility of the more stable form.

Method (ii) is a reaction crystallization in organic solvent(s) optionally containing a minor amount of water, with a buffering acidic salt of hydrobromic acid, preferably an amine salt of hydrobromic acid having a $pK_A$ of 3–7.5, and most preferably imidazole hydrobromide. The starting material is e.g. (R)-N-[5-methyl-8-(4-methylpiperazin-1-yl)-1,2,3,4-tetrahydro-2-naphtyl]-4-morpholinobenzamide or a salt different from (R)-N-[5-methyl-8-(4-methylpiperazin-1-yl)-1,2,3,4-tetrahydro-2-naphtyl]-4-morpholinobenzamide monohydrobromide. The composition of the resulting mixture after addition of the reactant should be such that it contains the ratio of organic solvent(s) optionally containing a minor amount of water required for formation of (R)-N-[5-methyl-8-(4-methylpiperazin-1-yl)-1,2,3,4-tetrahydro-2-naphtyl]-4-morpholinobenzamide monohydrobromide Form A. The crystallization may start spontaneously, but it is preferable to add seeds of (R)-N-[5-methyl-8-(4-methylpiperazin-1yl)-1,2,3,4-tetrahydro-2-naphtyl]-4-morpholinobenzamide monohydrobromide Form A.

Method (iii) is a crystallization from a solution of (R)-N-[5-methyl-8-(4-methylpiperazin-1-yl)-1,2,3,4-tetrahydro-2-naphtyl]-4-morpholinobenzamide monohydrobromide in a mixture of organic solvent(s) and water. The starting solution of (R)-N-[5-methyl-8-(4-methylpiperazin-1-yl)-1,2,3,4-tetrahydro-2-naphtyl]-4-morpholinobenzamide monohydrobromide might have been formed either by dissolution of already isolated (R)-N-[5-methyl-8-(4-methylpiperazin-1-yl)-1,2,3,4-tetrahydro-2-naphtyl]-4-morpholinobenzamide monohydrobromide, or might have been formed in a previous process step where (R)-N-[5-methyl-8-(4-methylpiperazin-1-yl)-1,2,3,4-tetrahydro-2-naphtyl]-4-morpholinobenzamide monohydrobromide has been formed by a chemical reaction. The solution may become supersaturated with respect to (R)-N-[5-methyl-8-(4-methylpiperazin-1-yl)-1,2,3,4-tetrahydro-2-naphtyl]-4-morpholinobenzamide monohydrobromide Form A due to the lower solubility of this form and crystallization of (R)-N-[5-methyl-8-(4-methylpiperazin-1-yl)-1,2,3,4- tetrahydro-2-naphtyl]-4-morpholinobenzamide monohydrobromide Form A can therefore occur spontaneously. However, if the original solution is undersaturated with respect to (R)-N-[5-methyl-8-(4-methylpiperazin-1-yl)-1,2,3,4-tetrahydro-2-naphtyl]-4-morpholinobenzamide monohydrobromide Form A, crystallization may be induced by decreasing the solubility of (R)-N-[5-methyl-8-(4-methylpiperazin-1-yl)-1,2,3,4-tetrahydro-2-naphtyl]-4-morpholinobenzamide monohydrobromide Form A in the system e.g. by cooling the mixture, by evaporating some of the solvents or by mixing with, e.g. by adding, some precipitating solvent. The water content in the final mixture is critical, but adjustment to the required solvent/water ratio can be done at any time in the process, e.g. before or during mixing with a precipitating solvent.

When the starting material for the crystallization of (R)-N-[5-methyl-8-(4-methylpiperazin-1-yl)-1,2,3,4-tetrahydro-2-naphtyl]-4-morpholinobenzamide monohydrobromide is an already isolated (R)-N-[5-methyl-8-(4-methylpiperazin-1-yl)-1,2,3,4-tetrahydro-2-naphtyl]-4-morpholinobenzamide monohydrobromide (for instance amorphous material or Form B), the process can be described in more detail as follows:

(R)-N-[5-methyl-8-(4-methylpiperazin-1-yl)-1,2,3,4-tetrahydro-2-naphtyl]-4-morpholinobenzamide monohydrobromide is dissolved in one or more organic solvents, preferably polar organic solvents, most preferably ethanol. In order to dissolve the starting material completely, it may be helpful to warm up the solvents or to add a small amount of water to the solvent system. The preferred amount of solvent mixture is 2–20 ml/g of (R)-N-[5-methyl-8-(4-methylpiperazin-1-yl)-1,2,3,4-tetrahydro-2-naphtyl]-4-morpholinobenzamide monohydrobromide, most preferably 3–15 ml/g. It is preferable that the total mixture is agitated, e.g. stirred, during dissolution. Water may be added before or during mixing with a precipitating solvent. It is preferable to add all the required water before mixing with the precipitating solvent, the ratio of water to organic solvent prior to addition of precipitating solvent in the resulting solvent system being from 1:1000 to 1:2, preferably 1:1000 to 1:20, depending on the organic solvents.

The crystallization of (R)-N-[5-methyl-8-(4-methylpiperazin-1-yl)-1,2,3,4-tetrahydro-2-naphtyl]-4-morpholinobenzamide monohydrobromide Form A may be obtained by mixing with a specific precipitating solvent at a temperature up to the boiling point of the specific solvent mixture. It is preferred that the temperature of the mixture during mixing with the precipitating solvent is 0 to +80° C., most preferably +20° C. to +75° C., and for the precipitating solvent preferably to be at ambient temperature before mixing. It is preferred to add the precipitating solvent to the (R)-N-[5-methyl-8-(4-methylpiperazin-1-yl)-1,2,3,4-tetrahydro-2-naphthy]-4-morpholinobenzamide monohydrobromide solution. The precipitation solvent may be added continuously or discontinuously, preferably continuously over a period of up to 12 hours. As the precipitating solvent, an organic solvent may be used, preferably a nonpolar solvent, e.g. acetone, ethyl methyl ketone, isobutyl methyl ketone, methyl acetate, ethyl acetate, isopropyl acetate, most preferably ethyl acetate. The amount of precipitating solvent should be such that the concentration of (R)-N-[5-methyl-8-(4-methylpiperazin-1-yl)-1,2,3,4-tetrahydro-2-naphtyl]-4-morpholinobenzamide monohydrobromide in the resulting mixture is higher than the solubility. The preferred ratio of precipitating solvent to the (R)-N-[5-methyl-8-(4-methylpiperazin-1-yl)-1,2,3,4-tetrahydro-2-naphtyl]-4-morpholinobenzamide monohydrobromide solution should be in the range of 1:1 to 10:1 by volume. The water content in the final mixture should preferably be below 5% by volume or otherwise the yield will be unacceptably low or the desired (R)-N-[5-methyl-8-(4-methylpiperazin-1-yl)-1,2,3,4-tetrahydro-2-naphtyl]-4-morpholinobenzamide monohydrobromide Form A may not be formed.

The crystallization may start spontaneously but it has frequently been found desirable to add seeds of (R)-N-[5-methyl-8-(4-methylpiperazin-1-yl)-1,2,3,4-tetrahydro-2-naphtyl]-4-morpholinobenzamide monohydrobromide Form A after the first addition of the precipitating solvent to induce crystallization and to obtain a higher crystallization rate and thus a shorter process time. Mixing, e.g. agitation, is preferable both during mixing of the precipitating solvent and the (R)-N-[5-methyl-8-(4-methylpiperazin-1-yl)-1,2,3,4-tetrahydro-2-naphtyl]-4-morpholinobenzamide monohydrobromide solution and during the crystallization process. The crystallization should continue for a period to ensure that crystallization is as complete as possible, e.g. 1 to 30 hours, preferably 5 to 12 hours.

The (R)-N-[5-methyl-8-(4-methylpiperazin-1-yl)-1,2,3,4-tetrahydro-2-naphtyl]-4-morpholinobenzamide monohydrobromide Form A crystals may be separated from the solution, e.g. by filtration or centrifugation, followed by washing with a washing liquid, preferably a solvent mixture in which (R)-N-[5-methyl-8-(4-methylpiperazin-1-yl)-1,2,3,4-tetrahydro-2-naphtyl]-4-morpholinobenzamide monohydrobromide Form A has a very low solubility, most preferably the precipitating solvent. The preferred ratio of washing liquid to the amount of product is 1:1 to 10:1 by weight. It is preferable to cool the slurry to below room temperature before separation of the crystals. The separated (R)-N-[5-methyl-8-(4-methylpiperazin-1-yl)-1,2,3,4-tetrahydro-2-naphtyl]-4-morpholinobenzamide monohydrobromide Form A crystals should be dried to constant weight, e.g. at +30° C. to +60° C., preferably at reduced pressure, for, e.g. 10 to 120 hours. The product from the precipitation process may comprise crystalline rods, needles or agglomerates or a mixture of rods, needles and agglomerates of (R)-N-[5-methyl-8-(4-methylpiperazin-1-yl)-1,2,3,4-tetrahydro-2-naphtyl]-4-morpholinobenzamide monohydrobromide Form A.

The above disclosed methods for preparation of (R)-N-[5-methyl-8-(4-methylpiperazin-1-yl)-1,2,3,4-tetrahydro-2-naphtyl]-4-morpholinobenzamide monohydrobromide Form A are reproducible and give a substantially pure and crystalline substance. The process of crystallization of (R)-N-[5-methyl-8-(4-methylpiperazin-1-yl)-1,2,3,4-tetrahydro-2-naphtyl]-4-morpholinobenzamide monohydrobromide Form A fulfils pharmaceutical criteria and specifications and may reduce batch to batch variability of drug in e.g. crystallinity. Filtration and drying conditions are favourable for (R)-N-[5-methyl-8-(4-methylpiperazin-1-yl)-1,2,3,4-tetrahydro-2-naphtyl]-4-morpholinobenzamide monohydrobromide Form A.

In a further aspect, the invention provides a compound obtainable by a process as described above, or, in a broader sense, (R)-N-[5-methyl-8-(4-methylpiperazin-1-yl)-1,2,3,4-tetrahydro-2-naphtyl]-4-morpholinobenzamide monohydrobromide Form A comprising such a compound.

Medical use of (R)-N-[5-methyl-8-(4-methylpiperazin-1-yl)-1,2,3,4-tetrahydro-2-naphtyl]-4-morpholinobenzamide monohydrobromide Form A In a further aspect the present invention provides the use of (R)-N-[5-methyl-8-(4-methylpiperazin-1-yl)-1,2,3,4- tetrahydro-2-naphtyl]-4-morpholinobenzamide monohydrobromide Form A in therapy as a h5-HT $_{1B}$ antagonist or partial agonist for the treatment or prevention of disorders in the central nervous system (CNS), e.g. in the treatment or prevention of 5-hydroxytryptamine mediated disorders and medical disturbances. It can for example be used in mood disorders, especially episodes of major depression, dysthymia, seasonal affective disorder, depressive phases of bipolar disorder, anxiety disorders such as obsessive compulsive disorder, panic disorder with/without agoraphobia, social phobia, specific phobia, generalized anxiety disorder, posttraumatic stress disorder, disorders of impulse control, e.g. trichotellomania, personality disorders, sleep disorders, eating disorders, e.g. obesity, anorexia, bulimia, premenstrual syndrome including premenstrual dysphoric disorder, sexual disturbances, abuse and/or dependence disorders, e.g. alcoholism, nicotine, autism, attention deficit disorder, hyperactivity disorder, migraine, memory disorders, e.g. age associated memory impairment, presenile and senile dementia such as Alzeheimer's disease, vascular dementia, pathological aggression, schizophrenia, endocrine disorders, e.g. hyperprolactinaemia, stroke, dyskinesia, Parkinson's disease, disorders of thermoregulation, pain, hypertension, over active bladder such as over active bladder, urinary incontinence, detrusor instability, neurogenic bladder, detrusor hyperreflexia, nocturnal enurisis, e.g. bed-wetting, in children, urinary frequency, urinary urgency, urge incontinence, stress incontinence, mixed incontinence, unstable bladder secondary to prostatitis or interstitial cystitis, vasospasm and growth control of tumors, e.g. lung carcinoma.

Pharmaceutical Formulations

In another aspect, the invention relates to pharmaceutical compositions comprising (R)-N-[5-methyl-8-(4-methylpiperazin-1-yl)-1,2,3,4-tetrahydro-2-naphtyl]-4-morpholinobenzamide monohydrobromide Form A as active ingredient optionally in association with diluents, excipients or inert carriers.

(R)-N-[5-methyl-8-(4-methylpiperazin-1-yl)-1,2,3,4-tetrahydro-2-naphtyl]-4-morpholinobenzamide monohydrobromide Form a may be formulated for administration in a convenient way and the invention includes all pharmaceutical compositions comprising this particular crystal form adapted for use in human medicine. Oral administration is preferable but other types of administration such as rectal or parenteral (dermal, nasal, tracheal, bronchial, or via inhalation route) administration are of interest.

Examples of formulations are tablets, capsules, pellets, granules, suspensions, solutions and suppositories, which formulations can have immediate-release or modified-release properties. The pharmaceutical compositions are prepared by techniques, which are known per se. Preferably, each daily dose of the active ingredient in an amount of 1 mg to 400 mg, and may be administered 1 to 4 times per day.

EXAMPLES OF THE INVENTION

Example 1

Preparation of (R)-N-[5-methyl-8-(4-methylpiperazin-1-yl)-1,2,3,4-tetrahydro-2-naphtyl]-4-morpholinobenzamide monohydrobromide Form A from (R)-N-[5-methyl-8-(4-methylpiperazin-1-yl)-1,2,3,4-tetrahydro-2-naphtyl]-4-morpholinobenzamide by reaction crystallisation:

To a slurry of (R)-N-[5-methyl-8-(4-methylpiperazin-1-yl)-1,2,3,4-tetrahydro-2-naphtyl]-4-morpholinobenzamide in ethanol (493 g, 1.1 mole, 2.5 L) is added a mixture of imidazole (82 g, 1.2 mole) and HBr in acetic acid (33 w/w %, 124 g, 1.5 mole) in ethanol (2.5 L) at 65° C. After the addition of all the material is dissolved, the solution is filtered clear and then heated at 80° C. for 2 h. The reaction mixture is then cooled to 65° C. and seeding crystals of (R)-N-[5-methyl-8-(4-methylpiperazin-1-yl)-1,2,3,4-tetrahydro-2-naphtyl]-4-morpholinobenzamide monohydrobromide Form A are added. From 65° C. a cooling profile is started with a cooling rate of 7–8° C./h until the temperature is −10° C. The slurry is then stirred for 8 hrs at −10° C. before the crystals are filtered off and washed with cool ethanol. Drying under vacuum (50° C.) gives 533 g (92%) of (R)-N-[5-methyl-8-(4-methylpiperazin-1-yl)-1,2,3,4-tetrahydro-2-naphtyl]-4-morpholinobenzamide monohydrobromide Form A; $^1$H NMR (300 MHz, DMSO-d$_6$) δ 8.24 (d, J=7.5 Hz, 1 H), 7.86 (d, J=8 Hz, 2 H), 6.92–7.08 (m, 1 H), 7.01 (d, J=7.5 Hz, 1 H), 6.98 (d, J=8 Hz, 1 H), 6.86 (d, J=8 Hz, 1 H), 3.61–4.07 (m, 5 H), 2.42–3.61 (m, 16 H), 2.84 (s, 3 H), 2.00–2.20 (m, 1 H), 2.15 (s, 3 H), 1.63–1.88 (m, 1 H). For further characterization, see below.

Example 2

Preparation of (R)-N-[5-methyl-8-(4-methylpiperazin-1-yl)-1,2,3,4-tetrahydro-2-naphtyl]-4-morpholinobenzamide monohydrobromide Form A by transformation in a slurry:

Crude (R)-N-[5-methyl-8-(4-methylpiperazin-1-yl)-1,2,3,4-tetrahydro-2-naphtyl]-4-morpholinobenzamide monohydrobromide (10.0 kg, 20.6 moles) is stirred in isopropanol (IPA, 80 L) at 60° C. for 19 hrs and then cooled to room temperature before filtration. Drying under vacuum at 50° C. gives 10.8 kg (99% yield) of pure (R)-N-[5-methyl-8-(4-methylpiperazin-1-yl)-1,2,3,4-tetrahydro-2-naphtyl]-4-morpholinobenzamide monohydrobromide Form A.

Example 3

Preparation of (R)-N-[5-methyl-8-(4-methylpiperazin-1-yl)-1,2,3,4-tetrahydro-2-naphtyl]-4-morpholinobenzamide monohydrobromide Form A by recrystallization of crude (R)-N-[5-methyl-8-(4-methylpiperazin-1-yl)-1,2,3,4-tetrahydro-2-naphtyl]-4-morpholinobenzamide monohydrobromide:

To crude (R)-N-[5-methyl-8-(4-methylpiperazin-1-yl)-1,2,3,4-tetrahydro-2-naphtyl]-4-morpholinobenzamide monohydrobromide (98 g, 0.22 mole) is added ethanol (0.57 L) and water (28.5 ml) at room temperature and a slurry is obtained. The slurry is then heated to 80° C. at which all solids are dissolved. The solution is then cooled to 70° C. before slowly adding ethyl acetate (0.25 L) to the solution. Seeding crystals of (R)-N-[5-methyl-8-(4-methylpiperazin-1-yl)-1,2,3,4-tetrahydro-2-naphtyl]-4-morpholinobenzamide monohydrobromide Form A are added followed by the addition of ethyl acetate (1.15 L) and the solution is cooled to −10° C. over 6 h. The slurry is stirred at −10° C. for 5 h before the crystals are filtered off. Drying under vacuum at 50° C. gives 88 g of pure (R)-N-[5-methyl-8-(4-methylpiperazin-1-yl)-1,2,3,4-tetrahydro-2-naphtyl]-4-morpholinobenzamide monohydrobromide Form A.

EXAMPLE OF A METHOD FOR GENERATING ANOTHER CRYSTAL MODIFICATION FORM OF (R)-N-[5-METHYL-8-(4-METHYLPIPERAZIN-1-YL)-1,2,3,4-TETRAHYDRO-2-NAPHTYL]-4-MORPHOLINOBENZAMIDE MONOHYDROBROMIDE

Preparation of (R)-N-[5-methyl-8-(4-methylpiperazin-1-yl)-1,2,3,4-tetrahydro-2-naphtyl]-4-morpholinobenzamide monohydrobromide Form B from crude (R)-N-[5-methyl-8-(4-methylpiperazin-1-yl)-1,2,3,4-tetrahydro-2-naphtyl]-4-morpholinobenzamide monohydrobromide:

To crude (R)-N-[5-methyl-8-(4-methylpiperazin-1-yl)-1,2,3,4-tetrahydro-2-naphtyl]-4-morpholinobenzamide monohydrobromide (0.8 g, 1.5 mmole) is added ethanol (18 ml) and everything is dissolves at 70° C. The solution is then cooled to 5° C. and stirred at 5° C. for 2.5 hrs. The crystals are filtered off and dried at 40° C. under vacuum. This gives 0.7 g (R)-N-[5-methyl-8-(4-methylpiperazin-1-yl)-1,2,3,4-tetrahydro-2-naphtyl]-4-morpholinobenzamide monohydrobromide Form B.

CHARACTERISATION OF (R)-N-[5-METHYL-8-(4-METHYLPIPERAZIN-1-YL)-1,2,3,4-TETRAHYDRO-2-NAPHTYL]-4-MORPHOLINOBENZAMIDE MONOHYDROBROMIDE FORMS A AND B

X-ray Powder Diffraction (XRPD)

X-ray diffraction analysis was performed according to standard methods, which can be found in e.g. Kitaigorodsky, A. I. (1973), Molecular Crystals and Molecules, Academic Press, New York; Bunn C. W. (1948), Chemical Crystallography, Clarendon Press, London; or Klug, H. P. & Alexander, L. E. (1974), X-ray Diffraction Procedures, John Wiley & Sons, New York.

The X-ray powder diffraction (XRPD) patterns of (R)-N-[5-methyl-8-(4-methylpiperazin-1-yl)-1,2,3,4-tetrahydro-2-naphtyl]-4-morpholinobenzamide monohydrobromide Forms A and B, obtained in Bragg-Brentano geometry, are shown in FIGS. 1 and 2.

The d-values and relative intensities are shown in Table 1. Both forms are highly crystalline as judged from the XRPD diffractograms.

TABLE 1

X-ray powder diffraction d-values and relative intensities, calculated as obtained with fixed slits, for (R)-N-[5-methyl-8-(4-methylpiperazin-1-yl)-1,2,3,4-tetrahydro-2-naphtyl]4-morpholinobenzamide monohydrobromide Forms A and B. Relative intensities are defined as very strong (vs) above 50% relative intensity, as strong (s) between 25–50%, as medium (m) between 10–25%, as weak (w) between 5–10% and as very weak (vw) up to 5%.

| Form A | | Form B | |
| --- | --- | --- | --- |
| d-value (Å) | Relative intensity | d-value (Å) | Relative intensity |
| 11.7 | vs | 14.7 | vw |
| 10.9 | s | 8.9 | vs |
| 8.0 | w | 7.9 | vw |
| 7.4 | m | 7.3 | m |
| 7.1 | w | 6.6 | m |
| 6.3 | w | 6.2 | vs |
| 6.2 | s | 5.9 | w |
| 5.9 | s | 5.8 | s |
| 5.8 | vw | 5.6 | vs |
| 5.6 | m | 4.97 | m |
| 5.5 | vw | 4.87 | s |
| 5.4 | m | 4.68 | w |
| 5.3 | vs | 4.64 | w |
| 5.1 | vw | 4.44 | s |
| 5.1 | m | 4.41 | s |
| 4.95 | vs | 4.37 | m |
| 4.82 | s | 4.33 | m |
| 4.71 | w | 4.24 | w |
| 4.60 | s | 4.19 | m |
| 4.56 | vs | 4.09 | m |
| 4.45 | vs | 3.96 | vs |
| 4.28 | vw | 3.89 | w |
| 4.24 | vw | 3.82 | s |

TABLE 1-continued

X-ray powder diffraction d-values and relative intensities, calculated as obtained with fixed slits, for (R)-N-[5-methyl-8-(4-methylpiperazin-1-yl)-1,2,3,4-tetrahydro-2-naphtyl]4-morpholinobenzamide monohydrobromide Forms A and B. Relative intensities are defined as very strong (vs) above 50% relative intensity, as strong (s) between 25–50%, as medium (m) between 10–25%, as weak (w) between 5–10% and as very weak (vw) up to 5%.

| Form A | | Form B | |
| --- | --- | --- | --- |
| d-value (Å) | Relative intensity | d-value (Å) | Relative intensity |
| 4.16 | vw | 3.77 | s |
| 4.10 | s | 3.65 | w |
| 3.99 | w | 3.56 | s |
| 3.96 | m | 3.50 | w |
| 3.92 | vs | 3.48 | m |
| 3.89 | m | 3.43 | w |
| 3.83 | m | 3.38 | m |
| 3.80 | s | 3.32 | w |
| 3.71 | m | 3.26 | w |
| 3.67 | m | 3.22 | m |
| 3.65 | m | 3.12 | w |
| 3.61 | vw | 3.09 | w |
| 3.57 | vw | 3.04 | w |
| 3.54 | w | 3.02 | vw |
| 3.50 | m | 2.97 | w |
| 3.45 | s | 2.93 | w |
| 3.39 | m | 2.86 | w |
| 3.31 | s | 2.77 | vw |
| 3.21 | m | 2.65 | vw |
| 3.17 | m | 2.55 | vw |
| 3.11 | m | 2.49 | vw |
| 3.09 | w | 2.41 | vw |
| 3.03 | w | 2.37 | vw |
| 2.97 | w | 2.34 | w |
| 2.90 | m | 2.31 | vw |
| 2.87 | w | | |
| 2.82 | vw | | |
| 2.79 | vw | | |
| 2.74 | w | | |
| 2.71 | w | | |
| 2.66 | w | | |
| 2.64 | vw | | |
| 2.61 | vw | | |
| 2.58 | vw | | |
| 2.53 | vw | | |
| 2.48 | vw | | |
| 2.41 | vw | | |
| 2.39 | vw | | |
| 2.38 | vw | | |
| 2.36 | vw | | |
| 2.34 | vw | | |
| 2.28 | vw | | |
| 2.27 | vw | | |

The XRPD-data for (R)-N-[5-methyl-8-(4-methylpiperazin-1-yl)-1,2,3,4-tetrahydro-2-naphtyl]-4-morpholinobenzamide monohydrobromide Form A may be fitted to a primitive orthorhombic unit cell with cell dimensions
a=21,88 Å
b=23,37 Å
c=10,13 Å

The space group, as determined from systematic absences is $P2_12_12_1$. The volume of the unit cell is 5180 Å$^3$.

The XRPD-data may for (R)-N-[5-methyl-8-(4-methylpiperazin-1-yl)-1,2,3,4-tetrahydro-2-naphtyl]-4-morpholinobenzamide monohydrobromide Form B (monohydrate) may be fitted to a primitive orthorhombic unit cell with cell dimensions
a=9,89 Å
b=29,23 Å
c=9,40 Å

The volume of the unit cell is 2720 Å$^3$.

(R)-N-[5-methyl-8-(4-methylpiperazin-1-yl)-1,2,3,4-tetrahydro-2-naphtyl]-4-morpholinobenzamide monohydrobromide Form A was found to be an anhydrate by thermal gravimetric analysis (TGA). Furthermore, it does not sorb essential amounts of water as measured by dynamic vapour sorption (DVS), 0,8% at 80% RH and 25° C.

(R)-N-[5-methyl-8-(4-methylpiperazin-1-yl)-1,2,3,4-tetrahydro-2-naphtyl]-4-morpholinobenzamide monohydrobromide Form B was found to be a monohydrate using a combination of TGA and DVS analysis. Karl Fischer titration verifies the presence of water. Although form B can desorb water when dried, leading to another crystal modification, it readily resorbs water again giving form B back.

STABILITY

The stability of [5-Methyl-8-(4-methylpiperazin-1-yl)-1,2,3,4-tetrahydro-2-naphtyl]-4-morpholinobenzamide (="Base" in tables below) and (R)-N-[5-methyl-8-(4-methylpiperazin-1-yl)-1,2,3,4-tetrahydro-2-naphtyl]-4-morpholinobenzamide monohydrobromide Form A (="Form A" in tables below), as bulk drug substance and in solutions at different pH levels after exposure to daylight and at elevated temperatures, has been studied.

RESULT SUMMARY

The results for the stability of drug substance are presented in Table 2. The bulk substances are very stable, both in daylight and at 90° C. There are no significant differences between the HPLC purity of [5-Methyl-8-(4-methylpiperazin-1-yl)-1,2,3,4-tetrahydro-2-naphtyl]-4-morpholinobenzamide (=Base) and (R)-N-[5-methyl-8-(4-methylpiperazin-1-yl)-1,2,3,4-tetrahydro-2-naphtyl]-4-morpholinobenzamide monohydrobromide Form A (=Form A) at the tested conditions.

Three solutions were made from each batch of drug substance. One solution in pure water, one in 0.1 mM HCl (pH 4.1) and one in 0.1 M HCl (pH 1.1). The content of [5-Methyl-8-(4-methylpiperazin-1-yl)-1,2,3,4-tetrahydro-2-naphtyl]-4-morpholinobenzamide (=Base) was determined by HPLC, all results are calculated as the base. The results are presented in Tables 3–5 below.

The stability at pH 1.1 and pH 4.1 is good and equal for both [5-Methyl-8-(4-methylpiperazin-1-yl)-1,2,3,4-tetrahydro-2-naphtyl]-4-morpholinobenzamide (=Base) and (R)-N-[5-methyl-8-(4-methylpiperazin-1-yl)-1,2,3,4-tetrahydro-2-naphtyl]-4-morpholinobenzamide monohydrobromide Form A (=Form A), except at 60° C. where the Base is less stable than Form A (more pronounced at pH 4.1 than at pH 1.1).

In the pure water solutions (pH was not adjusted), the Base is less stable than Form A at room temperature. The 60° C. condition is the only case where the salt is less stable than the Base.

The conclusion is that from a chemical stability point of view (R)-N-[5-methyl-8-(4-methylpiperazin-1-yl)-1,2,3,4-tetrahydro-2-naphtyl]-4-morpholinobenzamide monohydrobromide Form A (=Form A) is more stable or equal to [5-Methyl-8-(4-methylpiperazin-1-yl)-1,2,3,4-tetrahydro-2-naphtyl]-4-morpholinobenzamide (=Base) in all solutions tested (except for the water solution at 60° C.). The bulk stability towards temperature and daylight are equal for both [5-Methyl-8-(4-methylpiperazin-1-yl)-1,2,3,4-tetrahydro-2-naphtyl]-4-morpholinobenzamide (=Base) and (R)-N-[5-methyl-8-(4-methylpiperazin-1-yl)-1,2,3,4-tetrahydro-2-naphtyl]-4-morpholinobenzamide monohydrobromide Form A (=Form A).

TABLE 2

Stability of drug substance HPLC Purity (100% -related substances). RT is room temperature.

| Time | Base daylight, RT | Form A daylight, RT | Base 90° C. | Form A 90° C. |
|---|---|---|---|---|
| Start | 100% | 99.7% | 100% | 99.7% |
| 2 days | n.a | n.a. | 99.9% | 99.6% |
| 8 days | 99.9% | 99.6% | 99.9% | 99.6% |
| 14 days | 99.9% | 99.5% | 99.9% | 99.5% |
| 21 days | 99.9% | 99.5% | 99.9% | 99.6% |
| 30 days | 99.9% | 99.5% | 99.9% | 99.4% |

TABLE 3

Stability in water solutions, assay, all values are mg base/ml.

| Time | Base daylight RT | Form A daylight, RT | Base Dark RT | Form A Dark RT | Base 60° C. | Form A 60° C. | Base 5° C. | Form A 5° C. |
|---|---|---|---|---|---|---|---|---|
| Start | 0.00698 (100%) | 0.0248 (100%) | 0.00698 (100%) | 0.0248 (100%) | 0.00698 (100%) | 0.0248 (100%) | 0.00698 (100%) | 0.0248 (100%) |
| 2 days | n.a | n.a | n.a | n.a | 105% | 84% | n.a | n.a |
| 8 days | 95% | 100% | 94% | 99% | 104% | 81% | 101% | 101% |
| 14 days | 94% | 101% | 94% | 99% | 106% | 76% | 101% | 100% |
| 23 days | 91% | 100% | 95% | 97% | 102% | 82% | 102% | 99% |

TABLE 4

Solution in 0.1 mM HCl, pH 4.1, assay, all values are mg base/ml

| Time | Base daylight, RT | Form A daylight, RT | Base Dark RT | Form A Dark RT | Base 60° C. | Form A 60° C. | Base 5° C. | Form A 5° C. |
|---|---|---|---|---|---|---|---|---|
| Start | 0.0443 (100%) | 0.0490 (100%) | 0.0443 (100%) | 0.0490 (100%) | 0.0443 (100%) | 0.0490 (100%) | 0.0443 (100%) | 0.0490 (100%) |
| 2 days | n.a | n.a | n.a | n.a | 96% | 97% | n.a | n.a |

TABLE 4-continued

Solution in 0.1 mM HCl, pH 4.1, assay, all values are mg base/ml

| Time | Base daylight, RT | Form A daylight, RT | Base Dark RT | Form A Dark RT | Base 60° C. | Form A 60° C. | Base 5° C. | Form A 5° C. |
|---|---|---|---|---|---|---|---|---|
| 8 days | n.a | n.a | 99% | 99% | 93% | 93% | 100% | 100% |
| 14 days | 98% | 99% | 98% | 99% | 67% | 90% | 99% | 100% |
| 23 days | 98% | 97% | 97% | 98% | 57% | 81% | 99% | 100% |

TABLE 5

Solution in 0.1 M HCl, pH 1.1, assay, all values are mg base/ml

| Time | Base daylight, RT | Form A daylight, RT | Base Dark RT | Form A Dark RT | Base 60° C. | Form A 60° C. | Base 5° C. | Form A 5° C. |
|---|---|---|---|---|---|---|---|---|
| Start | 0.479 (100%) | 0.504 (100%) | 0.479 (100%) | 0.504 (100%) | 0.479 (100%) | 0.504 (100%) | 0.479 (100%) | 0.504 (100%) |
| 2 days | n.a | n.a | n.a | n.a | 98% | 100% | n.a | n.a |
| 8 days | n.a | n.a | 100% | 101% | 96% | 97% | 99% | 100% |
| 14 days | 100% | 100% | 100% | 99% | 91% | 95% | 100% | 100% |
| 23 days | 98% | 98% | 98% | 98% | 83% | 88% | 97% | 98% |

Solubility in Water

The solubility in water for (R)-N-[5-methyl-8-(4-methylpiperazin-1-yl)-1,2,3,4-tetrahydro-2-naphtyl]-4-morpholinobenzamide monohydrobromide Form A was determined to be 6.4 mg/mL as the free base by HPLC-analysis, which is satisfactory for pharmaceutical formulations. The solubility for (R)-N-[5-methyl-8-(4-methylpiperazin-1-yl)-1,2,3,4-tetrahydro-2-naphtyl]-4-morpholinobenzamide is 0.034 mg/mL under the same conditions.

Conclusions

The solid state characterization shows that (R)-N-[5-methyl-8-(4-methylpiperazin-1-yl)-1,2,3,4-tetrahydro-2-naphtyl]-4-morpholinobenzamide monohydrobromide Form A is crystalline, non-hygroscopic and has a satisfactory solubility in water. The chemical stability of drug substance as bulk and in solutions at different pH levels after exposure to daylight and at elevated temperatures, has been studied. From these experiments it can be concluded that (R)-N-[5-methyl-8-(4-methylpiperazin-1-yl)-1,2,3,4-tetrahydro-2-naphtyl]-4-morpholinobenzamide monohydrobromide Form A has at least the same stability as (R)-N-[5-methyl-8-(4-methylpiperazin-1-yl)-1,2,3,4-tetrahydro-2-naphtyl]-4-morpholinobenzamide with the exception of water solutions at 60° C.

What is claimed is:

1. (R)-N-[5-methyl-8-(4-methylpiperazin-1-yl)-1,2,3,4-tetrahydro-2-naphtyl]-4-morpholinobenzamide monohydrobromide Form A.

2. (R)-N-[5-methyl-8-(4-methylpiperazin-1-yl)-1,2,3,4-tetrahydro-2-naphtyl]-4-morpholinobenzamide monohydrobromide Form A according to claim 1, wherein the compound is substantially crystallographically pure.

3. (R)-N-[5-methyl-8-(4-methylpiperazin-1-yl)-1,2,3,4-tetrahydro-2-naphtyl]-4-morpholinobenzamide monohydrobromide Form A according to claim 2, wherein the compound contains not more than 10% of any other crystalline form of (R)-N-[5-methyl-8-(4-methylpiperazin-1-yl)-1,2,3,4-tetrahydro-2-naphtyl]-4-morpholinobenzamide monohydrobromide.

4. (R)-N-[5-methyl-8-(4-methylpiperazin-1-yl)-1,2,3,4-tetrahydro-2-naphtyl]-4-morpholinobenzamide monohydrobromide Form A according to claim 1, having an X-ray powder diffraction pattern exhibiting substantially the following d-values and relative intensities:

| Form A | | | | | |
|---|---|---|---|---|---|
| d-value (Å) | Relative intensity | d-value (Å) | Relative intensity | d-value (Å) | Relative intensity |
| 11.7 | vs | 4.24 | vw | 3.09 | w |
| 10.9 | s | 4.16 | vw | 3.03 | w |
| 8.0 | w | 4.10 | s | 2.97 | w |
| 7.4 | m | 3.99 | w | 2.90 | m |
| 7.1 | w | 3.96 | m | 2.87 | w |
| 6.3 | w | 3.92 | vs | 2.82 | vw |
| 6.2 | s | 3.89 | m | 2.79 | vw |
| 5.9 | s | 3.83 | m | 2.74 | w |
| 5.8 | vw | 3.80 | s | 2.71 | w |
| 5.6 | m | 3.71 | m | 2.66 | w |
| 5.5 | vw | 3.67 | m | 2.64 | vw |
| 5.4 | m | 3.65 | m | 2.61 | vw |
| 5.3 | vs | 3.61 | vw | 2.58 | vw |
| 5.1 | vw | 3.57 | vw | 2.53 | vw |
| 5.1 | m | 3.54 | w | 2.48 | vw |
| 4.95 | vs | 3.50 | m | 2.41 | vw |
| 4.82 | s | 3.45 | s | 2.39 | vw |
| 4.71 | w | 3.39 | m | 2.38 | vw |
| 4.60 | s | 3.31 | s | 2.36 | vw |
| 4.56 | vs | 3.21 | m | 2.34 | vw |
| 4.45 | vs | 3.17 | m | 2.28 | vw |
| 4.28 | vw | 3.11 | m | 2.27 | vw |

5. A process for the preparation of (R)-N-[5-methyl-8-(4-methylpiperazin-1-yl)-1,2,3,4-tetrahydro-2-naphtyl]-4-morpholinobenzamide monohydrobromide Form A according to claim 1, comprising partly dissolving non-Form A of (R)-N-[5-methyl-8-(4-methylpiperazin-1-yl)-1,2,3,4-tetrahydro-2-naphtyl]-4-morpholinobenzamide monohydrobromide in one or more organic solvents optionally containing a minor amount of water and stirring until Form A is obtained.

6. The process according to claim 5, wherein the non-A form of (R)-N-[5-methyl-8-(4-methylpiperazin-1-yl)-1,2,3,4-tetrahydro-2-naphtyl]-4-morpholinobenzamide monohydrobromide is an amorphous material, or is (R)-N-[5- methyl-8-(4-methylpiperazin-1-yl)-1,2,3,4-tetrahydro-2-naphtyl]-4-morpholinobenzamide monohydrobromide Form B.

7. A process for the preparation of (R)-N-[5-methyl-8-(4-methylpiperazin-1-yl)-1,2,3,4-tetrahydro-2-naphtyl]-4-morpholinobenzamide monohydrobromide Form A according to claim 1, comprising reaction crystallizing non-Form A (R)-N-[5-methyl-8-(4-methylpiperazin-1-yl)-1,2,3,4-tetrahydro-2-naphtyl]-4-morpholinobenzamide or a non-monohydrobromide salt of (R)-N-[5-methyl-8-(4-methylpiperazin-1-yl)-1,2,3,4-tetrahydro-2-naphtyl]-4-morpholinobenzamide with a buffering acidic salt of hydrobromic acid in one or more organic solvents optionally containing a minor amount of water to obtain crystals of (R)-N-[5-methyl-8-(4-methylpiperazin-1-yl)-1,2,3,4-tetrahydro-2-naphtyl]-4-morpholinobenzamide monohydrobromide Form A.

8. The process according to claim 7, wherein the buffering acidic salt of hydrobromic acid is imidazole hydrobromide.

9. A process for the preparation of (R)-N-[5-methyl-8-(4-methylpiperazin-1-yl)-1,2,3,4-tetrahydro-2-naphthyl]-4-morpholinobenzamide monohydrobromide Form A according to claim 1, comprising crystallizing from a solution of non-Form A (R)-N-[5-methyl-8-(4-methylpiperazin-1-yl)-1,2,3,4-tetrahydro-2-naphthyl]-4-morpholinobenzamide monohydrobromide in a mixture of one or more organic solvents and water, optionally followed by one or more steps selected from: 1) cooling the mixture; 2) evaporating a portion of the solvent; and 3) mixing with a precipitating solvent, to obtain crystals of (R)-N-[5-methyl-8-(4-methylpiperazin-1-yl)-1,2,3,4-tetrahydro-2-naphthyl]-4-morpholinobenzamide monohydrobromide Form A.

10. A pharmaceutical formulation comprising as active ingredient a therapeutically effective amount of the compound according to any one of claims 1–4, and optionally diluents, excipients, or inert carriers.

11. A method of treatment of a 5-hydroxytryptamine mediated disorder which comprises administering a therapeutically effective amount of the compound according to any one of claims 1–4, to a patient suffering from the 5-hydroxytryptamine mediated disorder.

12. A method for the treatment of a disorder selected from the group consisting of disorders in the central nervous system, overactive bladder, and vasospasm; or for growth control of tumors, comprising administering to a patient in need of such a treatment a therapeutically effective amount of the compound according to any one of claims 1–4.

13. The method according to claim 11, wherein the 5-hydroxytryptamine-mediated disorder is selected from the group consisting of mood disorders, anxiety disorders, personality disorders, obesity, anorexia, bulimia, pre-menstrual syndrome, sexual disturbances, alcoholism, tobacco abuse, autism, attention deficit, hyperactivity disorders, migraine, memory disorders, pathological aggression, schizophrenia, endocrine disorders, stroke, dyskinesia, Parkinson's disease, thermoregulatory disorders, pain, or hypertension.

14. The process according to claim 7, wherein the buffering acidic salt of hydrobromic acid is an amine salt of hydrobromic acid having a $pK_A$ of 3–7.5.

15. The process according to claim 9, wherein the non-Form A of (R)-N-[5-methyl-8-(4-methylpiperazin-1-yl)-1,2,3,4-tetrahydro-2-naphtyl]-4-morpholinobenzamide monohydrobromide is formed by dissolution of previously isolated (R)-N-[5-methyl-8-(4-methylpiperazin-1-yl)-1,2,3,4-tetrahydro-2-naphtyl]-4-morpholinobenzamide monohydrobromide, or is formed in a previous process step by a chemical reaction.

16. The process according to any one of claims 5, 7, or 9, wherein the organic solvent is ethanol.

17. The process according to claim 9, wherein the precipitating solvent is ethyl acetate.

* * * * *

UNITED STATES PATENT AND TRADEMARK OFFICE
CERTIFICATE OF CORRECTION

PATENT NO. : 6,706,710 B2
DATED : March 16, 2004
INVENTOR(S) : Bergström et al.

It is certified that error appears in the above-identified patent and that said Letters Patent is hereby corrected as shown below:

<u>Title page</u>,
Insert Item:
-- [30]  Foreign Application Priority Data
July 20, 2000  (SE)...0002729-2 --.

Signed and Sealed this

Seventeenth Day of August, 2004

JON W. DUDAS
*Acting Director of the United States Patent and Trademark Office*